US011176441B2

(12) United States Patent
Aggarwal et al.

(10) Patent No.: US 11,176,441 B2
(45) Date of Patent: Nov. 16, 2021

(54) NEURAL NETWORK ARCHITECTURE FOR PERFORMING MEDICAL CODING

(71) Applicant: International Business Machines Corporation, Armonk, NY (US)

(72) Inventors: Nitish Aggarwal, San Jose, CA (US); Sheng Hua Bao, San Jose, CA (US); Pathirage Perera, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 870 days.

(21) Appl. No.: 15/967,886

(22) Filed: May 1, 2018

(65) Prior Publication Data

US 2019/0340487 A1 Nov. 7, 2019

(51) Int. Cl.
*G06N 3/04* (2006.01)
*G06N 3/02* (2006.01)

(52) U.S. Cl.
CPC .............. *G06N 3/04* (2013.01); *G06N 3/02* (2013.01)

(58) Field of Classification Search
CPC .. G06N 3/02; G06N 3/04; G06N 3/08; G16H 10/60; G16H 70/20; G16H 70/60
See application file for complete search history.

(56) References Cited

U.S. PATENT DOCUMENTS

| 9,589,374 | B1 | 3/2017 | Gao et al. |
| 2016/0093048 | A1 | 3/2016 | Cheng et al. |

FOREIGN PATENT DOCUMENTS

WO    WO 2017/151759 A1    9/2017

OTHER PUBLICATIONS

Schroll, Jeppe Bennekou et al.; Challenges in Coding Adverse Events in Clinical Trials: A Systematic Review; PLoS One, Jul. 2012, vol. 7, Issue 7, ed41174; pp. 1-7. (Year: 2012).*
Morley, Greg; Adverse event reporting: A brief overview of MedDRA; The European Medical Writers Association; Medical Writing 2014 vol. 23 No. 2; pp. 113-116. (Year: 2014).*
Mullenbach, James et al.; Explainable Prediction of Medical Codes from Clinical Text; 2018 Georgia Institute of Technology; 11 pages. (Year: 2018).*

(Continued)

*Primary Examiner* — Stanley K. Hill
(74) *Attorney, Agent, or Firm* — Stephen J. Walder, Jr.; William J. Stock

(57) ABSTRACT

Mechanisms are provided to implement a medical coding engine to perform medical coding using a neural network architecture that leverages hierarchical semantics between medical concepts. The medical coding engine configures a medical coding neural network to comprise an first layer of nodes comprising preferred terminology (PT) nodes, a second layer comprising lowest level terminology (LLT) nodes, and a third layer comprising weighted values for each connection between each PT node and each LLT node forming a PT node/LLT node connection. Responsive to receiving an adverse event from a cognitive system, a PT node is identified in the first layer associated with a citation from the adverse event. One or more nodes are identified from the second layer based on the identification PT node and a weight associated with the PT node/LLT node connection. A medical code associated with each the one or more LLT nodes is then output.

20 Claims, 5 Drawing Sheets

(56) References Cited

OTHER PUBLICATIONS

Latif, Jahanzaib et al.; Implementation and Use of Disease Diagnosis Systems for Electronic Medical Records Based on Machine Learning: A Complete Review; 2020; IEEE Access, vol. 8, pp. 150489-150513. (Year: 2020).*
"Machine Learning for Hardware Simulation", Disclosed Anonymously, An IP.com Prior Art Database Technical Disclosure, IP.com No. IPCOM000251992D, Dec. 13, 2017, 33 pages.
"Modeling Disease Incidence and Progression Using Deep Neurai Networks", Disclosed Anonymously, An IP.com Prior Art Database Technical Disclosure, IP.com No. IPCOM000252181D, Dec. 20, 2017, 5 pages.
"Predictive Cryptocurrency Mining and Staking", Disclosed Anonymously, An IP.com Prior Art Database Technical Disclosure, IP.com No. IPCOM000252017D, Dec. 13, 2017, 34 pages.
De Vine, Lance et al., "Medical Semantic Similarity with a Neural Language Model", ACM, CIKM'14, Shanghai, China, Nov. 3-7, 2014, 4 pages.
Farkas, Richard et al., "Automatic construction of ruie-based ICD-9-CM coding systems", BMC Bioinformatics 2008, vol. 9 (Suppl 3):S10, Apr. 11, 2008, 9 pages.
Goldstein, Ira et al., "Three Approaches to Automatic Assignment of ICD-9-CM Codes to Radiology Reports", American Medical informatics Association, AMIA Annual Symposium Proceedings, vol. 2007, Oct. 11, 2007, pp. 279-283.
Harispe, Sébastien et al., "Semantic Similarity from Natural Language and Ontology analysis", arXiv preprint, arXiv:1704.05295v1, Apr. 18, 2017, 175 pages.
High, Rob, "The Era of Cognitive Systems: An Inside Look at IBM Watson and How it Works", IBM Corporation, Redbooks, Dec. 12, 2012, 16 pages.
Mencía, Eneldo L. et al., "Medical Concept Embeddings via Labeled Background Corpora", European Language Resources Association (ELRA), Proceedings of the 10th Language Resources and Evaluation Conference (LREC 2016), Portorož, Slovenia, May 23-26, 2016, pp. 4629-4636.
Pakhomov, Serguei V. et al., "Automating the Assignment of Diagnosis Codes to Patient Encounters Using Example-based and Machine Learning Techniques", Journal of the American Medical Informatics Association, vol. 13, No. 5, Sep./Oct. 2006, pp. 516-525.
Pereira, Suzanne et al., "Construction of a semi-automated ICD-10 coding help system to optimize medical and economic coding", IOS Press, Medical Informatics Europe, vol. 124, Jan. 1, 2006, pp. 845-850.

* cited by examiner

NEURAL NETWORK ARCHITECTURE FOR PERFORMING MEDICAL CODING

BACKGROUND

The present application relates generally to an improved data processing apparatus and method and more specifically to mechanisms for performing medical coding using a neural network architecture that leverages hierarchical semantics between medical concepts in medical dictionaries.

Uniquely identifying medical concepts in healthcare data is a key task in many processes in healthcare domains. Coding adverse event citations to the Medical Dictionary for Regulatory Activities (MedDRA), coding drug citations to the WHO Drug Dictionary (WHO-DD), coding medical condition citations to the International Classification of Diseases and Related Health Problems (10th edition) (ICD-10) are few such examples. These coding tasks are inherently difficult due to the richness and the complexity of the healthcare domains. Consider the example of MedDRA coding; MedDRA is a highly specific and rich hierarchical dictionary with five levels characterizing the adverse events. The five levels from root to leaf nodes are named as System Organ Class, High Level Group Term, High Level Term, Preferred Term, and Lowest Level Term. The latest MedDRA dictionary has 76,468 lowest level terms. It is being used to map human reported adverse events to standard vocabulary facilitating the sharing of regulatory information internationally for medical products.

This mapping task is a challenging cognitive task for human practitioners even with pharma domain knowledge. This is due to the large number of possible codes and fine-grained semantic differences between the codes (the textual description of codes in leaf nodes has subtle differences). Traditionally, these coding tasks are carried out by the highly trained domain experts in the healthcare domain. More recently, solutions have been developed to automate these complex coding tasks. These solutions use different variations of string matching techniques, traditional learning-based techniques, rule-based techniques, information retrieval techniques, knowledge-based techniques, etc. to find the most appropriate codes for the medical concept citations. However, the complexity and diversity of the medical event citations challenges these current approaches. For example, it is noticed that traditional methods omit significant portions of the adverse event citations to the MedDRA dictionary terms.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising a processor and a memory, the memory comprising instructions that are executed by the processor to configure the processor to implement a medical coding engine to perform medical coding using a neural network architecture that leverages hierarchical semantics between medical concepts in medical dictionaries. The method comprises configuring a medical coding neural network to comprise a first layer of nodes comprising preferred terminology (PT) nodes representing preferred terminologies of a medical coding schema. The method also comprises configuring the medical coding neural network to comprise a second layer comprising lowest level terminology (LLT) nodes representing a lowest level terminologies of a medical coding schema. Moreover, the method comprises configuring the medical coding neural network to comprise a third layer between the first layer and the second layer comprising weighted values for each connection between each PT node in the first layer and each LLT node in the second layer forming a PT node/LLT node connection. In addition, the method comprises, responsive to receiving an adverse event from a cognitive system, identifying a PT node in the first layer associated with a citation from the adverse event. The method also comprises identifying one or more LLT nodes from the second layer based on the identification PT node and a weight associated with the PT node/LLT node connection. Additionally, the method comprises outputting a medical code associated with each the one or more LLT nodes.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
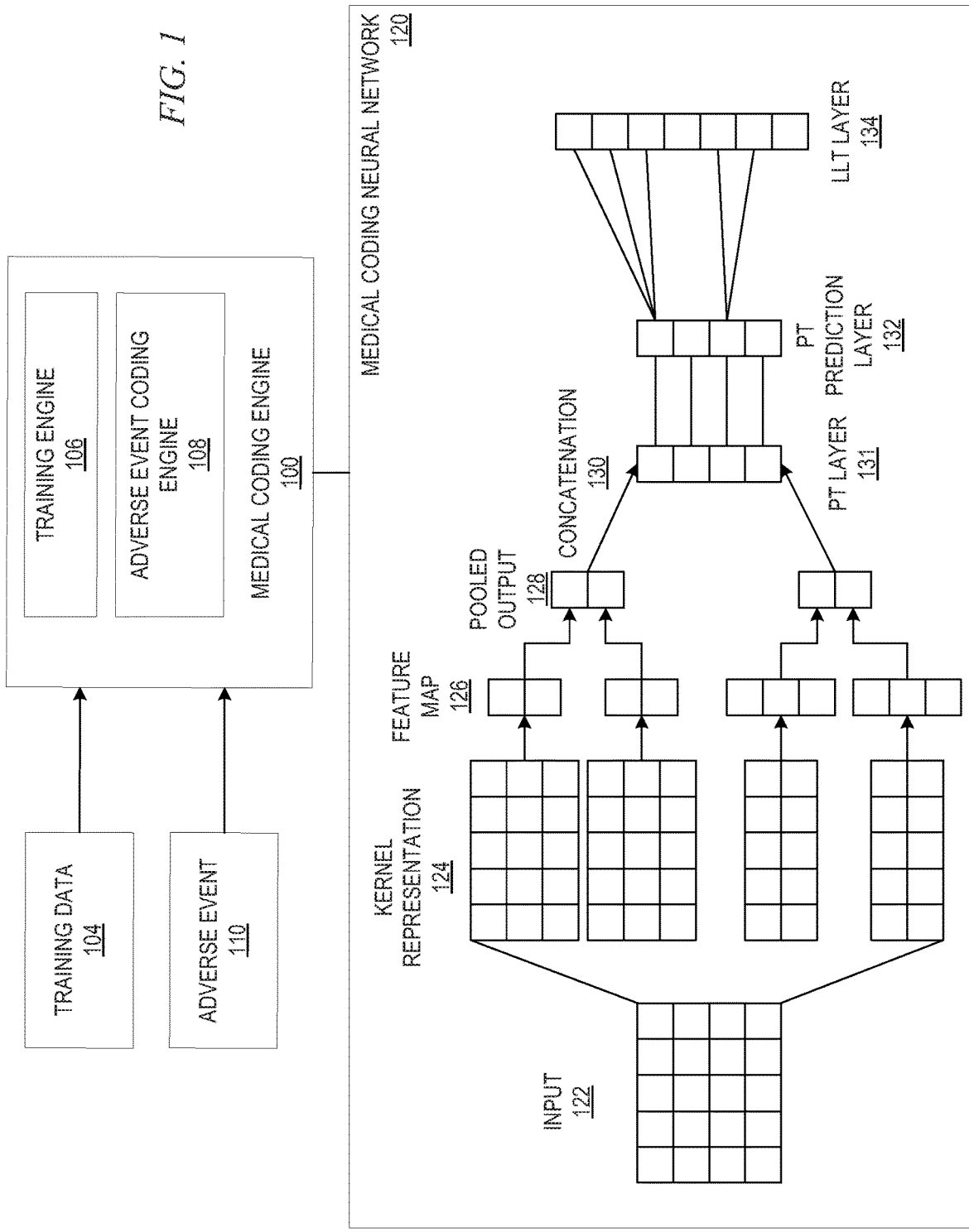
FIG. 1 is an example block diagram illustrating components of a medical coding engine in accordance with one illustrative embodiment.

The illustrative embodiments provide mechanisms for performing medical coding using a neural network architecture that leverages hierarchical semantics between medical concepts in medical dictionaries. That is, the mechanisms provide a neural network architecture that uses hierarchical semantics of medical dictionaries to increase the effective usage of labelled data for medical coding tasks, which improve the accuracy of such medical coding tasks over traditional learning-based solutions. The mechanisms exploit semantic similarities between medical event citations in electronic medical records (EMRs) of a patient and medical codes in a medical dictionary at a word and/or character level.

The mechanisms form a neural network that represents the hierarchical organization of the vocabulary. As noted previously, a number of nodes in a level of a medical dictionary increase as a hierarchy of the medical dictionary is traversed, for example, the latest MedDRA dictionary has 76,468 lowest level terms. Hence, the classification problem become challenging if the algorithm classifies incoming text to the leaf nodes directly. The mechanisms address this challenge by guiding the final prediction such that intermediate decisions are taken advantage of in a way that reflects the hierarchical structure of the vocabulary. Thus, the mechanisms influence code assignment by training the neural network by forming a deep-learning neural network to simultaneously predict two codes that have complementary semantic meaning, thereby increasing the coding accuracy. In other words, each medical event citation is assigned with two codes: the code on the leaf node and its parent—given that code and its parent has similar semantic meaning but only differs in the granularity level of description, where the simultaneous assignment complement each other. This essentially increases the effectiveness of the training data since each training data instance is used twice in the training process. This also increases the coding accuracy due to increased training data and extra guidance provided to assign leaf node through its parent.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present, To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the illustrative embodiments of the present invention provides a methodology, apparatus, system and computer program product for performing for performing medical coding using a medical coding neural network architecture that leverages hierarchical semantics between medical concepts in medical dictionaries. The following illustrates the operations of implementing a medical coding neural network to perform medical coding utilizing a MedDRA coding task. The MedDRA coding task aims to select a most appropriate leaf node in the MedDRA vocabulary hierarchy for an adverse event citation in a patient's electronic medical record (EMR). Essentially, the medical coding neural network is formed with layers of a System Organ Class, a High Level Group Term, a High Level Term, a Preferred Term, and a Lowest Level Term. However, the illustrative embodiments redesign the connections between the Preferred Term (PT) layer and the Lowest Level Term (LLT) layer. Whereas, in the current MedDRA hierarchy, each term or node in the PT layer is connected to each term or node in the LLT layer thereby forming a fully associative neural network layer, the illustrative embodiments change the connections between a node in the PT layer and nodes in the LLT layer such that a node in the PT layer is only coupled to a single node or a select few nodes in the LLT layer. Specifically, the illustrative embodiment change the connections between the LLT layer and the PT layer such that the nodes that represent the terms in the LLT layer are connected to only corresponding nodes that represent a relevant term in the PT layer, thereby forming a non-fully associative neural network layer.

In order to implement this improved medical coding neural network architecture, the illustrative embodiments provide a new PT prediction layer that assign weights to each connection between a node in the PT layer and a node in the LLT layer. In the PT prediction layer weights associated with each connection are initially set to an initialized weight value, such as zero, a randomly assigned value, or the like. Then, though training of verified PT node to LLT node associations, the illustrative embodiments increase a weight of a given PT node to LLT node connection in the PT prediction layer. For this given PT node to LLT node connection, further occurrences of the connection increases the weight of the connection. Thus, for the verified PT node to LLT node connections, a training of the medical coding neural network architecture increases the accuracy of future medical coding. That is, when a new adverse event is detected in a patient's EMR, the medical coding neural network traverses down to the PT layer. Upon identifying an appropriate node in the PT layer, the illustrative embodiments only consider connection(s) of the node in the PT layer to nodes in the LLT layer meeting a certain criteria, such as a highest weight, a weight above a predetermined threshold, or the like, as indicated in the PT predication layer as candidates for an appropriate LLT term for the adverse event. Therefore, rather than traversing 76,468 LLT nodes, the illustrative embodiment provide for the medical coding neural network with only having to traverse those LLT nodes with connections weighted above the predetermined threshold in the PT predication layer, which may be as little as one node. While the above illustration is with regard to a MedDRA hierarchy, the illustrative embodiments are not limited to only this hierarchy. That is, a similar predication layer may be implemented in any medical coding system without departing from the spirit and scope of the invention. Thus, the present invention provides a neural network architecture in which provides weighted links between nodes in different layers and limits consideration of terms in a lowest layer based on those weights and a predetermined threshold.

FIG. 1 is an example block diagram illustrating components of a medical coding engine in accordance with one illustrative embodiment. As shown in FIG. 1, medical coding engine 100 comprises training engine 102 and coding engine 104. The following utilizes MedDRA coding task as an example for the operations performed by medical coding engine. In order for medical coding engine 100 to more accurately and efficiently code adverse events identified by a cognitive system with which medical coding engine 100 operates, medical coding engine 100 initially trains novel Preferred Term (PT) prediction layer 132 of medical coding neural network 120. That is, training engine 106 uses training data 104 that may be obtained from a large corpus of annotated and labelled adverse events for MedDRA coding. The input to medical coding neural network 120 from medical coding engine 100 is then an adverse event text represented with low-dimensional embeddings of the words. Low-dimensional embedding is vector-based representation of text in a low dimension (~100) to make it understandable/processable by computing devices, such as medical coding neural network 120. The training process implemented by training engine 106 learns the correct weights for connections between PT and LLT nodes. That is, initially, each PT node to LLT node connection is initially set to an initialized weight value, such as zero, a randomly assigned value, or the like. Then, as the training occurs, training engine 106 increases a weight of the associated connection for each verified PT node to LLT node association. Training engine 106 continues the training for each PT node to LLT node association in training data 104. Training engine 106 stores the weighted connection values in PT prediction layer 132.

Thus, medical coding neural network 120 is configured to include PT prediction layer 132 between a last layer of nodes (Lowest Level Term (LLT) layer 134) representing a lowest level terminology of a medical coding schema and a PT layer 131 representing parent terminologies to the lowest level terminologies of the medical coding schema. PT prediction layer 132 stores associated weights for each PT node to LLT node connection or associated. Therefore, medical coding neural network 120 is configured as a non-fully associative neural network such that nodes of a first layer (PT layer 131) of the medical coding neural network are connected to only a selected subset of nodes of a next layer (LLT layer 134) in a non-fully associative manner.

Adverse event coding engine 108 then utilizes the weights that are stored in the PT prediction layer 132 for performing medical coding for an adverse event. That is, upon adverse event coding engine 108 receiving adverse event 110 detected in a patient's electronic medical record (EMR), adverse event coding engine 108 analyzes adverse event 110 at a word and/or character level. For each word and/or character, adverse event coding engine 108 generates kernel representations of the terms used in adverse event 110 thereby forming the kernel representation layer 124. Adverse event coding engine 108 then extracts feature maps from the kernel representations forming the feature maps in feature map layer 126. From the feature maps, adverse event coding engine 108 generates pooled outputs. Adverse event coding engine 108 then concatenates the pooled outputs to generate a concatenated vector in concatenation layer 130 that identifies a PT node in a PT layer 131.

Once at PT layer 131, adverse event coding engine 108 identifies an appropriate PT node in PT layer 131. In one embodiment, adverse event coding engine 108 identifies the connection from the node in PT layer 131 that has a highest weight to a LLT node in LLT layer 134. Thus, adverse event coding engine 108 identifies the PT node/LLT node connection with the highest weight and outputs a medical code corresponding to the LLT node in LLT layer 134 based on processing adverse event 110.

In another embodiment, adverse event coding engine 108 then identities connections from the node in PT layer 131 that have a weighted connection to LLT layer 134 above a predetermined threshold as indicated in PT predication layer 132. That is, only those connections from PT layer 131 to LLT layer 134 with weights above the predetermined threshold are considered as candidates for an appropriate LLT term for the adverse event. Thus, adverse event coding engine 108 identifies one or more PT node/LLT node connections above the predetermined threshold and outputs one or more medical codes corresponding to the LLT nodes associated with those connections based on processing adverse event 110.

Therefore, rather than traversing 76,468 LLT nodes as is the current number of LLT nodes in the current MedDRA, adverse event coding engine 108 only having to traverse those PT node/LLT node connections weighted above the predetermined threshold as indicated in PT predication layer 132, which may be as little as one node. While the above illustration is with regard to a MedDRA hierarchy, the illustrative embodiments are not limited to only this hierarchy. That is, a similar predication layer may be implemented in any medical coding system without departing from the spirit and scope of the invention. Thus, the present invention provides a neural network architecture in which provides weighted links between nodes in different layers and limits consideration of terms in a lowest layer based on those weights and a predetermined threshold.

As a further feature to the illustrative embodiments, training engine 106 may utilize the output of medical codes corresponding to the LLT nodes/PT code pair(s) based on processing adverse event 110 to modify the weights of PT node/LLT node connections in the medical coding neural network to minimize a loss function of the medical coding neural network thought a back-propagation process. That is, as each output is verified, training engine 106 uses the verified PT node/LLT node pair to increase the weight of the PT prediction in the PT predication layer 132 associated with that PT node/LLT node pair. In another embodiment, if the out provided by adverse event coding engine 106 is identified as in error, training engine 106 uses the faulty PT node/LLT node pair to decrease the weight of the PT prediction in the PT predication layer 132 associated with that PT node/LLT node pair.

Figure 2:
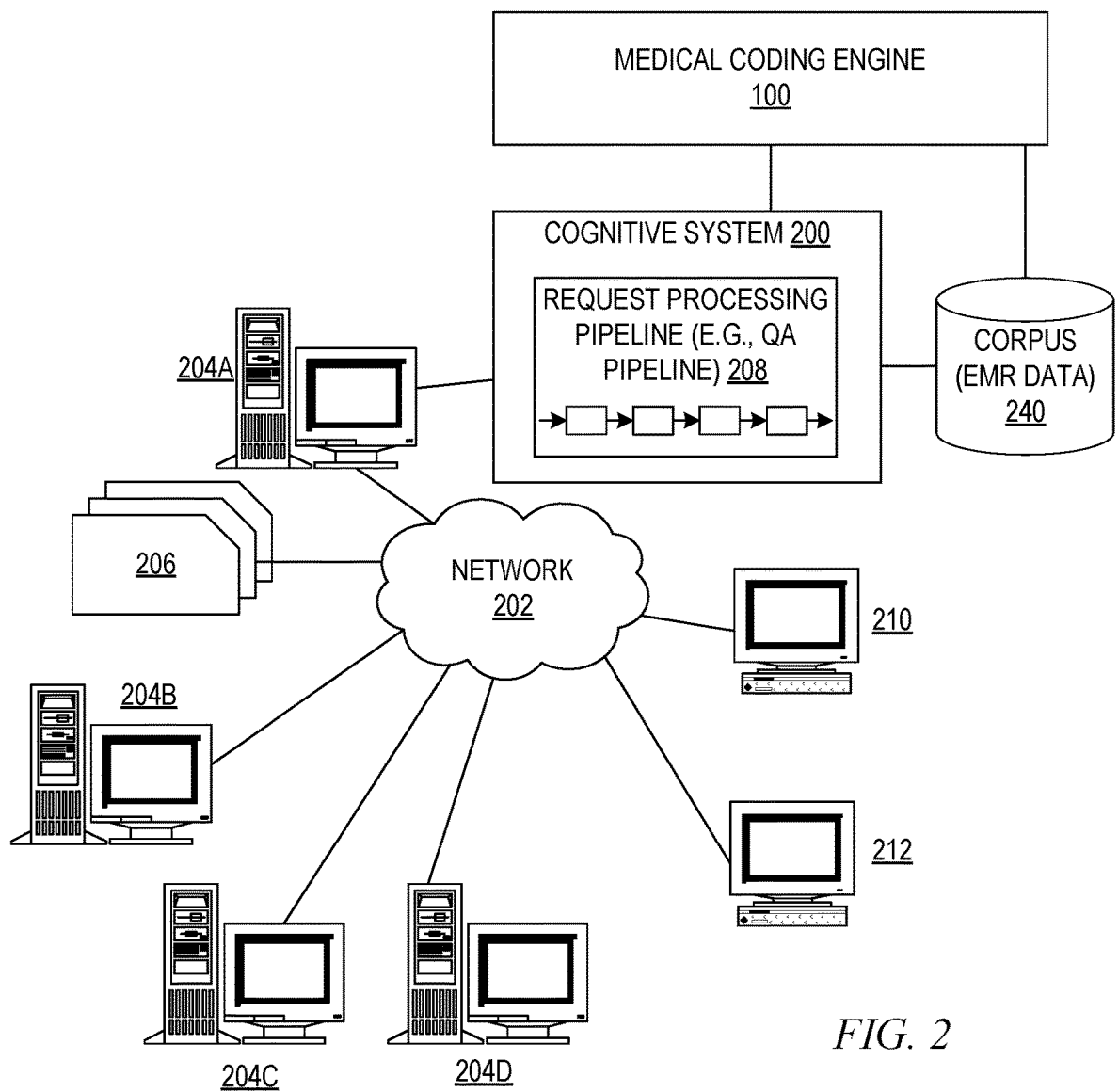
FIG. 2 depicts a schematic diagram of one illustrative embodiment of a cognitive healthcare system in a computer network.
Figure 3:
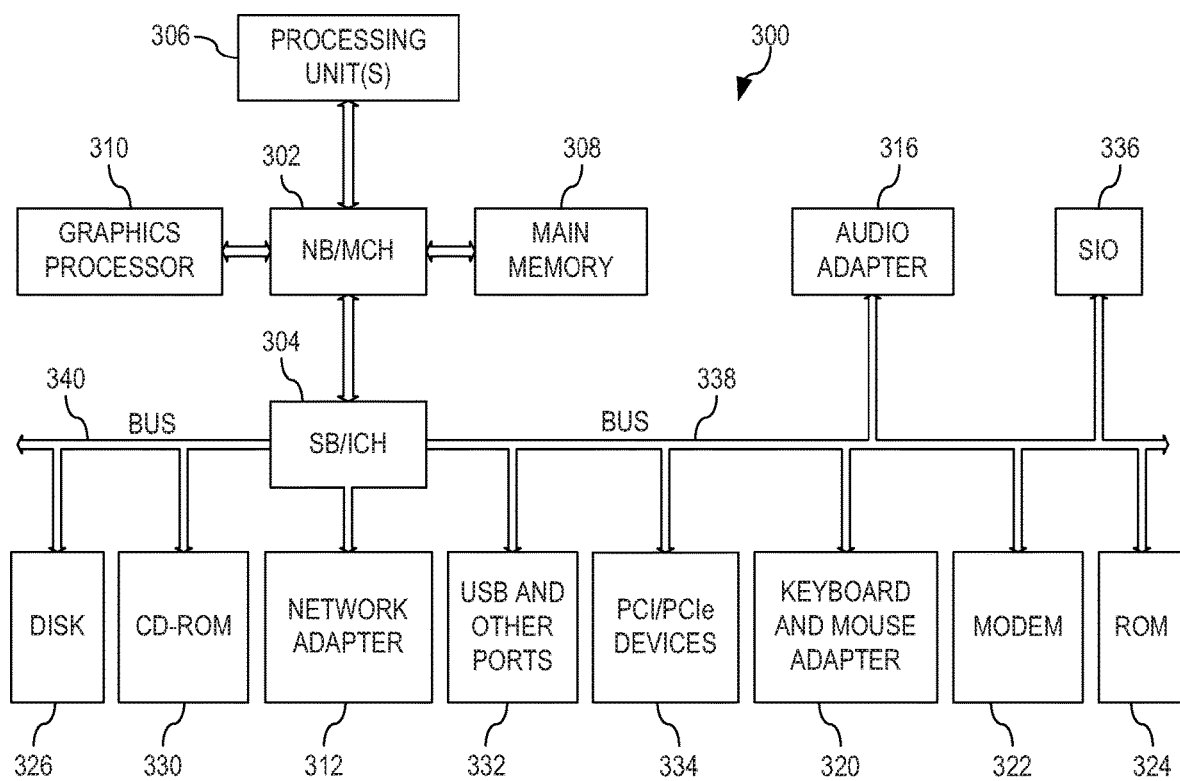
FIG. 3 is a block diagram of an example data processing system in which aspects of the illustrative embodiments are implemented.

It is clear from the above, that the illustrative embodiments may be utilized in many different types of data processing environments. In order to provide a context for the description of the specific elements and functionality of the illustrative embodiments, FIGS. 2-3 are provided hereafter as example environments in which aspects of the illustrative embodiments may be implemented. It should be appreciated that FIGS. 2-3 are only examples and are not intended to assert or imply any limitation with regard to the environments in which aspects or embodiments of the present invention may be implemented. Many modifications to the depicted environments may be made without departing from the spirit and scope of the present invention.

It should be noted that the mechanisms of the illustrative embodiments need not be utilized with a cognitive system. To the contrary, the illustrative embodiments may be implemented as a medical coding engine implemented on one or more computing devices or systems. The standalone medical coding engine may generate an output notification that may be utilized by a user when evaluating a particular adverse event. Thus, in a standalone implementation, the medical coding engine may be implemented using one or more computing devices or systems such as depicted in FIG. 3, as one example. However, to illustrate further functionality of illustrative embodiments of the present invention, FIGS. 2-3 are provided to illustrate the way in which the medical coding engine may be utilized with a cognitive system to perform cognitive healthcare operations for diagnosing or treating a patient.

FIGS. 2-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for performing medical coding using a neural network architecture that leverages hierarchical semantics between medical concepts in medical dictionaries by the medical coding engine of the illustrative embodiments.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

The request processing pipelines may utilize the analysis performed by the drug-adverse event causality evaluation engine of one or more of the illustrative embodiments, such as medical coding engine 100 in FIG. 1, as a factor considered by the request processing pipeline when performing cognitive evaluations of a patient to determine a diagnosis of the patient, determine a recommended treatment for the patient, and/or monitor the patient, with an aim at minimizing adverse drug reactions for drugs taken by the patient.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments for performing medical coding using a neural network architecture that leverages hierarchical semantics between medical concepts in medical dictionaries by the medical coding engine of the illustrative embodiments. It should be appreciated that while embodiments of the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 2-3 are only examples and are not intended to state or imply any limitation with regard to the type of cognitive system mechanisms with which the illustrative embodiments are implemented. Many modifications to the example cognitive system shown in FIGS. 2-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding,
Ingest and process vast amounts of structured and unstructured data,
Generate and evaluate hypothesis,
Weigh and evaluate responses that are based only on relevant evidence,
Provide situation-specific advice, insights, and guidance,
Improve knowledge and learn with each iteration and interaction through machine learning processes,
Enable decision making at the point of impact (contextual guidance),
Scale in proportion to the task,
Extend and magnify human expertise and cognition,
Identify resonating, human-like attributes and traits from natural language,
Deduce various language specific or agnostic attributes from natural language,
High degree of relevant recollection from data points (images, text, voice) (memorization and recall),
Predict and sense with situational awareness that mimic human cognition based on experiences, or
Answer questions based on natural language and specific evidence.

In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, al domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, types of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these questions and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest-ranking score or confidence measure, or which is a best match to the input question, or a combination of ranked listing and final answer.

With regard to the drug-adverse event causality evaluation engine of the illustrative embodiments, the recommendations generated by the drug-adverse event causality evaluation engine may be input to the QA pipeline for use as yet another portion of the corpus or corpora upon which the QA pipeline operates. For example, the recommendations generated by the drug-adverse event causality evaluation engine may be included in inputs upon which the operations of the reasoning algorithms are applied, as part of the evaluation of evidence supporting various candidate answers or responses generated by the QA pipeline, or the like. Thus, the reasoning algorithms may include factors for performing medical coding using a neural network architecture that leverages hierarchical semantics between medical concepts in medical dictionaries.

FIG. 2 depicts a schematic diagram of one illustrative embodiment of a cognitive system 200 implementing a request processing pipeline 208, which in some embodiments may be a question answering (QA) pipeline, in a computer network 202. For purposes of the present description, it will be assumed that the request processing pipeline 208 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 200 is implemented on one or more computing devices 204A-D (comprising one or more processors and one or more memories, and potentially any other computing device elements generally known in the art including buses, storage devices, communication interfaces, and the like) connected to the computer network 202. For purposes of illustration only, FIG. 2 depicts the cognitive system 200 being implemented on computing device 204A only, but as noted above the cognitive system 200 may be distributed across multiple computing devices, such as a plurality of computing devices 204A-D. The network 202 includes multiple computing devices 204A-D, which may operate as server computing devices, and 210-212 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 200 and network 202 enables question processing and answer generation (QA) functionality for one or more cognitive system users via their respective computing devices 210-212. In other embodiments, the cognitive system 200 and network 202 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 200 may be used with components, systems, subsystems, and/or devices other than those that are depicted herein.

The cognitive system 200 is configured to implement a request processing pipeline 208 that receive inputs from various sources. The requests may be posed in the form of a natural language question, natural language request for information, natural language request for the performance of a cognitive operation, or the like. For example, the cognitive system 200 receives input from the network 202, a corpus or corpora of electronic documents 206, cognitive system users, and/or other data and other possible sources of input. In one embodiment, some or all of the inputs to the cognitive system 200 are routed through the network 202. The various computing devices 204A-D on the network 202 include access points for content creators and cognitive system users. Some of the computing devices 204A-D includes devices for a database storing the corpus or corpora of data 206 (which is shown as a separate entity in FIG. 2 for illustrative purposes only). Portions of the corpus or corpora of data 206 may also be provided on one or more other network attached storage devices, in one or more databases, or other computing devices not explicitly shown in FIG. 2. The network 202 includes local network connections and remote connections in various embodiments, such that the cognitive system 200 may operate in environments of any size, including local and global, e.g., the Internet.

In one embodiment, the content creator creates content in a document of the corpus or corpora of data 206 for use as part of a corpus of data with the cognitive system 200. The document includes any file, text, article, or source of data for use in the cognitive system 200. Cognitive system users access the cognitive system 200 via a network connection or an Internet connection to the network 202, and input questions/requests to the cognitive system 200 that are answered/processed based on the content in the corpus or corpora of data 206. In one embodiment, the questions/requests are formed using natural language. The cognitive system 200 parses and interprets the question/request via a pipeline 208, and provides a response to the cognitive system user, e.g., cognitive system user 210, containing one or more answers to the question posed, response to the request, results of processing the request, or the like. In some embodiments, the cognitive system 200 provides a response to users in a ranked list of candidate answers/responses while in other illustrative embodiments, the cognitive system 200 provides a single final answer/response or a combination of a final answer/response and ranked listing of other candidate answers/responses.

The cognitive system 200 implements the pipeline 208 which comprises a plurality of stages for processing an input question/request based on information obtained from the corpus or corpora of data 206. The pipeline 208 generates answers/responses for the input question or request based on the processing of the input question/request and the corpus or corpora of data 206.

In some illustrative embodiments, the cognitive system 200 may be the BM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 206. Based on the application of the queries to the corpus or corpora of data 206, a set of hypotheses, or candidate answers/responses to the input question/request, are generated by looking across the corpus or corpora of data 206 for portions of the corpus or corpora of data 206 (hereafter referred to simply as the corpus 206) that have some potential for containing a valuable response to the input question/response (hereafter assumed to be an input question). The pipeline 208 of the IBM Watson™ cognitive system then performs deep analysis on the language of the input question and the language used in each of the portions of the corpus 206 found during the application of the queries using a variety of reasoning algorithms.

The scores obtained from the various reasoning algorithms are then weighted against a statistical model that summarizes a level of confidence that the pipeline 208 of the IBM Watson™ cognitive system 200, in this example, has regarding the evidence that the potential candidate answer is inferred by the question. This process is repeated for each of the candidate answers to generate a ranked listing of candidate answers which may then be presented to the user that submitted the input question, a user of client computing device 210, or from which a final answer is selected and presented to the user. More information about the pipeline 208 of the IBM Watson™ cognitive system 200 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 200 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result. In particular, the mechanisms of the healthcare based cognitive system may process drug-adverse events or adverse drug reaction pairings when performing the healthcare oriented cognitive system result, a diagnosis or treatment recommendation.

In the context of the present invention, cognitive system 200 may provide a cognitive functionality for assisting with healthcare based operations. For example, depending upon the particular implementation, the healthcare based operations may comprise patient diagnostics, medical treatment recommendation systems, personal patient care plan generation and monitoring, patient electronic medical record (EMR) evaluation for various purposes, such as for identifying patients that are suitable for a medical trial or a particular type of medical treatment, or the like. Thus, the cognitive system 200 may be a healthcare cognitive system 200 that operates in the medical or healthcare type domains and which may process requests for such healthcare operations via the request processing pipeline 208 input as either structured or unstructured requests, natural language input questions, or the like. In one illustrative embodiment, the cognitive system 200 is a medical treatment recommendation system that analyzes a patient's electronic medical records (EMRs) in relation to medical guidelines and other medical documentation in a corpus of information, and further performing medical coding using a neural network architecture that leverages hierarchical semantics between medical concepts in medical dictionaries.

As shown in FIG. 2, the cognitive system 200 is further augmented, in accordance with the mechanisms of the illustrative embodiments, to include logic implemented in specialized hardware, software executed on hardware, or any combination of specialized hardware and software executed on hardware, for implementing medical coding engine 100. As described previously, the medical coding engine 100 performs medical coding using a neural network architecture that leverages hierarchical semantics between medical concepts in medical dictionaries. Medical coding engine 100 identities an appropriate node in the PT layer and only considers connection(s) of the node in the PT layer to nodes in the LLT layer meeting a certain criteria, such as a highest weight, a weight above a predetermined threshold, or the like, as indicated in the PT predication layer as candidates for an appropriate LLT term for the adverse event. Medical coding engine 100 then outputs one or more medical codes corresponding to the LLT nodes associated with those PT node connections.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 3 is provided as an example of one type of data processing system in which aspects of the present invention may be implemented. Many other types of data processing systems may be likewise configured to specifically implement the mechanisms of the illustrative embodiments.

FIG. 3 is a block diagram of an example data processing system in which aspects of the illustrative embodiments are implemented. Data processing system 300 is an example of a computer, such as server 204A or client 210 in FIG. 2, in which computer usable code or instructions implementing the processes for illustrative embodiments of the present invention are located. In one illustrative embodiment, FIG. 3 represents a server computing device, such as a server 204, which, which implements a cognitive system 200 and QA system pipeline 208 augmented to include the additional mechanisms of the illustrative embodiments described hereafter.

In the depicted example, data processing system 300 employs a hub architecture including North Bridge and Memory Controller Hub (NB/MCH) 302 and South Bridge and Input/Output (I/O) Controller Hub (SB/ICH) 304. Processing unit 306, main memory 308, and graphics processor 310 are connected to NB/MCH 302, Graphics processor 310 is connected to NB/MCH 302 through an accelerated graphics port (AGP).

In the depicted example, local area network (LAN) adapter 312 connects to SB/ICH 304. Audio adapter 316, keyboard and mouse adapter 320, modem 322, read only memory (ROM) 324, hard disk drive (HDD) 326, CD-ROM drive 330, universal serial bus (USB) ports and other communication ports 332, and PCI/PCIe devices 334 connect to SB/ICH 304 through bus 338 and bus 340, PCI/PCIe devices may include, for example, Ethernet adapters, add-in cards, and PC cards for notebook computers. PCI uses a card bus controller, while PCIe does not. ROM 324 may be, for example, a flash basic input/output system (BIOS).

HDD 326 and CD-ROM drive 330 connect to SB/ICH 304 through bus 340. HDD 326 and CD-ROM drive 330 may use, for example, an integrated drive electronics (IDE) or serial advanced technology attachment (SATA) interface. Super I/O (SIO) device 336 is connected to SB/ICH 304.

An operating system runs on processing unit 306. The operating system coordinates and provides control of various components within the data processing system 300 in FIG. 3. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 300.

As a server, data processing system 300 may be, for example, an IBM® eServer™ System p® computer system, running the Advanced Interactive Executive (AIX®) operating system or the LINUX® operating system. Data processing system 300 may be a symmetric multiprocessor (SMP) system including a plurality of processors in processing unit 306. Alternatively, a single processor system may be employed.

Instructions for the operating system, the object-oriented programming system, and applications or programs are located on storage devices, such as HDD 326, and are loaded into main memory 308 for execution by processing unit 306. The processes for illustrative embodiments of the present invention are performed by processing unit 306 using computer usable program code, Which is located in a memory such as, for example, main memory 308, ROM 324, or in one or more peripheral devices 326 and 330, for example.

A bus system, such as bus 338 or bus 340 as shown in FIG. 3, is comprised of one or more buses. Of course, the bus system may be implemented using any type of communication fabric or architecture that provides for a transfer of data between different components or devices attached to the fabric or architecture. A communication unit, such as modem 322 or network adapter 312 of FIG. 3, includes one or more devices used to transmit and receive data. A memory may be, for example, main memory 308, ROM 324, or a cache such as found in NB/MCH 302 in FIG. 3.

Those of ordinary skill in the art will appreciate that the hardware depicted in FIGS. 2 and 3 may vary depending on the implementation. Other internal hardware or peripheral devices, such as flash memory, equivalent non-volatile memory, or optical disk drives and the like, may be used in addition to or in place of the hardware depicted in FIGS. 2 and 3. Also, the processes of the illustrative embodiments may be applied to a multiprocessor data processing system, other than the SMP system mentioned previously, without departing from the spirit and scope of the present invention.

Moreover, the data processing system 300 may take the form of any of a number of different data processing systems including client computing devices, server computing devices, a tablet computer, laptop computer, telephone or other communication device, a personal digital assistant (PDA), or the like. In some illustrative examples, data processing system 300 may be a portable computing device that is configured with flash memory to provide non-volatile memory for storing operating system files and/or user-generated data, for example. Essentially, data processing system 300 may be any known or later developed data processing system without architectural limitation.

Figure 4:
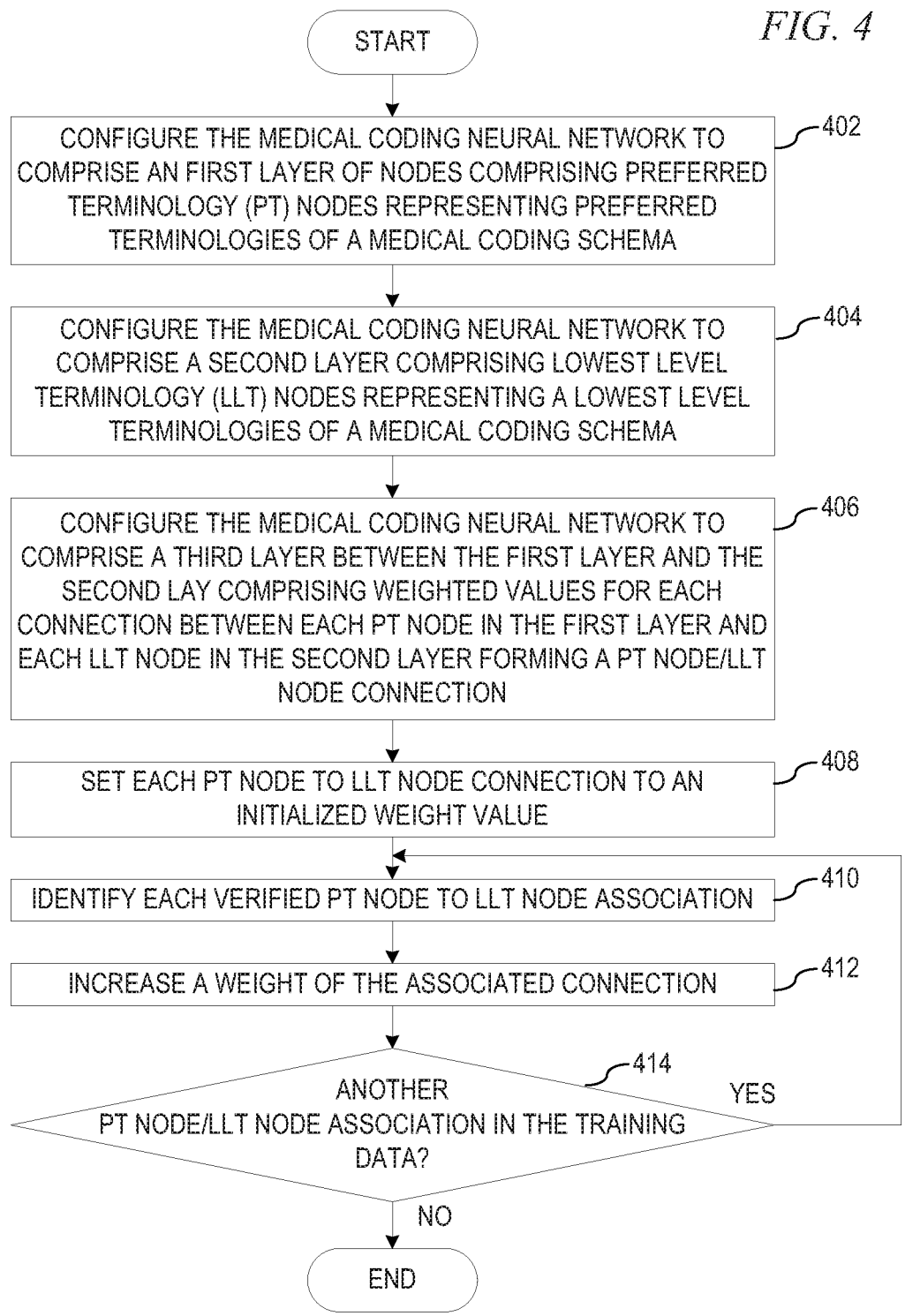
FIG. 4 is a flowchart outlining example operations performed by a medical coding engine in training a medical coding neural network in accordance with one illustrative embodiment.

FIG. 4 is a flowchart outlining example operations performed by a medical coding engine in training a medical coding neural network in accordance with one illustrative embodiment. As the exemplary operation begins, the medical coding engine configures the medical coding neural network to comprise a first layer of nodes comprising preferred terminology (PT) nodes representing preferred terminologies of a medical coding schema (step 402). The medical coding engine configures the medical coding neural network to comprise a second layer comprising lowest level terminology (LLT) nodes representing a lowest level terminologies of a medical coding schema (step 404). The medical coding engine configures the medical coding neural network to comprise a third layer between the first layer and the second layer comprising weighted values for each connection between each PT node in the first layer and each LLT node in the second layer forming a PT node/LLT node connection (step 406). The training engine initially sets each PT node to LLT node connection to an initialized weight value, such as zero, a randomly assigned value, or the like (step 408). Using training data, which may be obtained from a large corpus of annotated and labelled adverse events for MedDRA coding the training engine implements a training process implemented to learns the correct weights for connections between PT and LLT nodes. Thus, to learn the correct weights, the training engine identifies each verified PT node to LLT node association (step 410) and increase a weight of the associated connection (step 412), which is stored in a PT prediction layer. The training engine continues the training for each PT node to LLT node association in the training data. Thus, the training engine determined whether there is another PT node/LLT node association in the training data (step 414). If at step 414 there is another PT node/LLT node association, the operation returns to step 410. If at step 414 there is no other PT node/LLT node association, the operation terminates.

Figure 5:
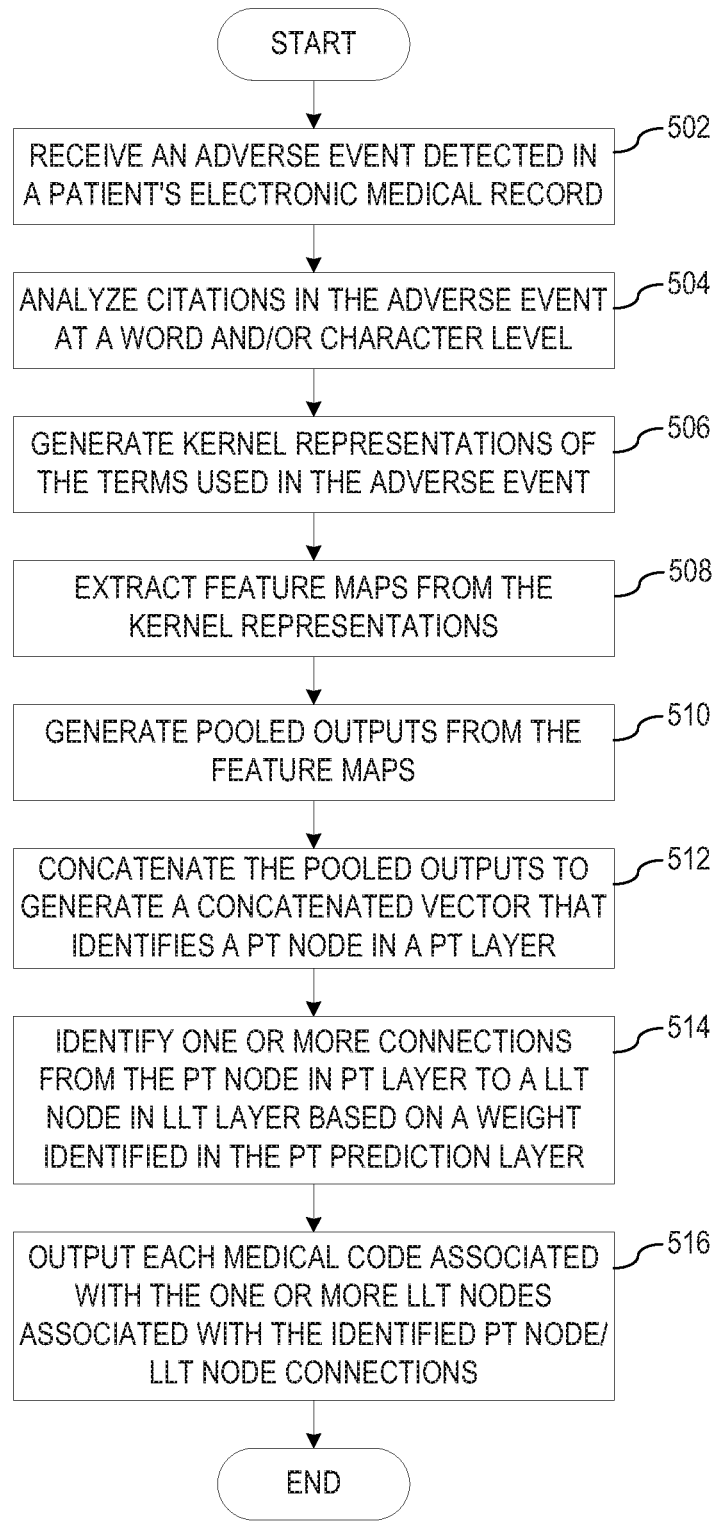
FIG. 5 is a flowchart outlining example operations performed by a medical coding engine in identifying one or more medical codes for an adverse event using the trained medical coding neural network in accordance with one illustrative embodiment.

FIG. 5 is a flowchart outlining example operations performed by a medical coding engine in identifying one or more medical codes for an adverse event using the trained medical coding neural network in accordance with one illustrative embodiment. As the operation begins, the medical coding engine receives an adverse event detected in a patient's electronic medical record (EMR) (step 502). The medical coding engine analyzes citations in the adverse event at a word and/or character level (step 504). For each word and/or character, medical coding engine generates kernel representations of the terms used in the adverse event (step 506). The medical coding engine extracts feature maps from the kernel representations (step 508) and generates pooled outputs from the feature maps (step 510). Medical coding engine then concatenates the pooled outputs to generate a concatenated vector that identifies a PT node in a PT layer (step 512). Once at PT layer, the medical coding engine identifies one or more connections from the PT node in PT layer to a LLT node in LLT layer based on a weight identified in the PT prediction layer (step 514). The medical coding engine then outputs each medical code associated with the one or more LLT nodes associated with the identified PT node/LLT node connections (step 516). The operation terminates thereafter.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions that are executed by the at least one processor to cause the at least one processor to be configured to implement a medical coding engine to perform medical coding using a neural network architecture that leverages hierarchical semantics between medical concepts in medical dictionaries, the method comprising:

configuring, by the medical coding engine, a medical coding neural network to comprise a first layer of nodes comprising preferred terminology (PT) nodes representing preferred terminologies of a medical coding schema;

configuring, by the medical coding engine, the medical coding neural network to comprise a second layer comprising lowest level terminology (LLT) nodes representing lowest level terminologies of a medical coding schema;

configuring, by the medical coding engine, the medical coding neural network to comprise a third layer between the first layer and the second layer comprising weighted values for each connection between each PT node in the first layer and each LLT node in the second layer forming a PT node/LLT node connection;

responsive to receiving an adverse event from a cognitive system, identifying, by the medical coding engine, a PT node in the first layer associated with a citation from the adverse event;

identifying, by the medical coding engine, one or more LLT nodes from the second layer based on the identification PT node and a weight associated with the PT node/LLT node connection; and outputting, by the medical coding engine, a medical code associated with each of the one or more LLT nodes.

2. The method of claim 1, wherein the weights associated with each PT node/LLT node connection is obtained by training the medical coding neural network to classify adverse event citations using verified PT node/LLT node associations thereby forming a trained medical coding neural network.

3. The method of claim 1, wherein the medical coding neural network is non-fully associative neural network such that each PT nodes in the first layer of the medical coding neural network is connected to only a selected subset of LLT nodes in the second layer.

4. The method of claim 1, wherein configuring the medical coding neural network to comprise connection that connect each PT node to corresponding LLT nodes further comprises setting an initial weight value of the connection to an initialized weight value.

5. The method of claim 1, wherein training the medical coding neural network further comprises using back-propagation to modify weights of PT node/LLT node connections to minimize a loss function of the medical coding neural network.

6. The method of claim 5, wherein a verified LLT node output increases a weight associated with the PT node/LLT node connection associated with the LLT node output.

7. The method of claim 5, wherein a false LLT node output decreases a weight associated with the PT node/LLT node connection associated with the LLT node output.

8. The method of claim 1, wherein the medical coding neural network processes the adverse event citation by:

generating, by medical coding neural network, kernel representations of the terms used in the adverse event citation;

extracting, by medical coding neural network, feature maps from the kernel representations;

generating, by medical coding neural network, a pooled output of the feature maps for each of the kernel representations;

concatenating, by medical coding neural network, the pooled outputs of the feature maps for each of the kernel representations to generate a concatenated vector input; and processing, by medical coding neural network, the concatenated vector input by the trained medical coding neural network to identify a PT node.

9. A computer program product comprising a computer readable storage medium having a computer readable program stored therein, wherein the computer readable program, when executed on a data processing system, causes the data processing system to implement a medical coding engine to perform medical coding using a neural network architecture that leverages hierarchical semantics between medical concepts in medical dictionaries, and further causes the data processing system to:

configure, by the medical coding engine, a medical coding neural network to comprise a first layer of nodes comprising preferred terminology (PT) nodes representing preferred terminologies of a medical coding schema;

configure, by the medical coding engine, the medical coding neural network to comprise a second layer comprising lowest level terminology (LLT) nodes representing lowest level terminologies of a medical coding schema;

configure, by the medical coding engine, the medical coding neural network to comprise a third layer between the first layer and the second layer comprising weighted values for each connection between each PT node in the first layer and each LLT node in the second layer forming a PT node/LLT node connection;

responsive to receiving an adverse event from a cognitive system, identify, by the medical coding engine, a PT node in the first layer associated with a citation from the adverse event;

identify, by the medical coding engine, one or more LLT nodes from the second layer based on the identification PT node and a weight associated with the PT node/LLT node connection; and output, by the medical coding engine, a medical code associated with each of the one or more LLT nodes.

10. The computer program product of claim 9, wherein the weights associated with each PT node/LLT node connection is obtained by training the medical coding neural network to classify adverse event citations using verified PT node/LLT node associations thereby forming a trained medical coding neural network.

11. The computer program product of claim 9, wherein the medical coding neural network is non-fully associative neural network such that each PT nodes in the first layer of the medical coding neural network is connected to only a selected subset of LLT nodes in the second layer.

12. The computer program product of claim 9, wherein configuring the medical coding neural network to comprise connection that connect each PT node to corresponding LLT nodes further comprises setting an initial weight value of the connection to an initialized weight value.

13. The computer program product of claim 9, wherein training the medical coding neural network further comprises using back-propagation to modify weights of PT node/LLT node connections to minimize a loss function of the medical coding neural network.

14. The computer program product of claim 13, wherein a verified LLT node output increases a weight associated with the PT node/LLT node connection associated with the LLT node output and wherein a false LLT node output decreases a weight associated with the PT node/LLT node connection associated with the LLT node output.

15. A data processing system comprising:
at least one processor; and
at least one memory coupled to the at least one processor, wherein the at least one memory comprises instructions which, when executed by the at least one processor, cause the at least one processor to implement a medical coding engine to perform medical coding using a neural network architecture that leverages hierarchical semantics between medical concepts in medical dictionaries, and further cause the at least one processor to:
configure, by the medical coding engine, a medical coding neural network to comprise a first layer of nodes comprising preferred terminology (PT) nodes representing preferred terminologies of a medical coding schema;
configure, by the medical coding engine, the medical coding neural network to comprise a second layer comprising lowest level terminology (LLT) nodes representing lowest level terminologies of a medical coding schema;
configure, by the medical coding engine, the medical coding neural network to comprise a third layer between the first layer and the second layer comprising weighted values for each connection between each PT node in the first layer and each LLT node in the second layer forming a PT node/LLT node connection;
responsive to receiving an adverse event from a cognitive system, identify, by the medical coding engine, a PT node in the first layer associated with a citation from the adverse event;
identify, by the medical coding engine, one or more LLT nodes from the second layer based on the identification PT node and a weight associated with the PT node/LLT node connection; and
output, by the medical coding engine, a medical code associated with each of the one or more LLT nodes.

16. The data processing system of claim 15, wherein the weights associated with each PT node/LLT node connection is obtained by training the medical coding neural network to classify adverse event citations using verified PT node/LLT node associations thereby forming a trained medical coding neural network.

17. The data processing system of claim 15, wherein the medical coding neural network is non-fully associative neural network such that each PT nodes in the first layer of the medical coding neural network is connected to only a selected subset of LLT nodes in the second layer.

18. The data processing system of claim 15, wherein configuring the medical coding neural network to comprise connection that connect each PT node to corresponding LLT nodes further comprises setting an initial weight value of the connection to an initialized weight value.

19. The data processing system of claim 15, wherein training the medical coding neural network further comprises using back-propagation to modify weights of PT node/LLT node connections to minimize a loss function of the medical coding neural network.

20. The data processing system of claim 19, wherein a verified LLT node output increases a weight associated with the PT node/LLT node connection associated with the LLT node output and wherein a false LLT node output decreases a weight associated with the PT node/LLT node connection associated with the LLT node output.

* * * * *